United States Patent
Bird

(10) Patent No.: US 6,595,203 B1
(45) Date of Patent: Jul. 22, 2003

(54) APPARATUS FOR ADMINISTERING INTERMITTENT PERCUSSIVE VENTILATION AND UNITARY BREATHING HEAD ASSEMBLY FOR USE THEREIN

(76) Inventor: Forrest M. Bird, 1655 Glengary Bay Rd., Sandpoint, ID (US) 83864

( * ) Notice: Subject to any disclaimer, the term of this patent is extended or adjusted under 35 U.S.C. 154(b) by 147 days.

(21) Appl. No.: 09/724,589

(22) Filed: Nov. 28, 2000

(51) Int. Cl.[7] .................. A61M 16/00; A61M 11/00
(52) U.S. Cl. ..................... 128/200.21; 128/200.14; 128/204.25; 239/338
(58) Field of Search ................. 128/204.18, 204.24, 128/204.25, 205.11, 203.25, 203.24, 203.14, 200.21, 200.22; 239/338, 370, 375, 367, 361

(56) References Cited

U.S. PATENT DOCUMENTS

| | | | | |
|---|---|---|---|---|
| 3,460,532 A | * | 8/1969 | Bird et al. | 128/145.6 |
| 3,537,448 A | * | 11/1970 | Listen | 128/145.5 |
| 3,769,973 A | * | 11/1973 | Esbenshade, Jr. | 128/200.1 |
| 4,323,064 A | | 4/1982 | Hoenig et al. | |
| 4,462,397 A | | 7/1984 | Suzuki | |
| 5,054,478 A | * | 10/1991 | Grychowski et al. | 128/200.14 |
| 5,119,807 A | | 6/1992 | Roberts | |
| 5,165,398 A | * | 11/1992 | Bird | 128/204.25 |
| 5,862,802 A | * | 1/1999 | Bird | 128/204.18 |
| 6,067,984 A | | 5/2000 | Piper | |

* cited by examiner

Primary Examiner—Weilun Lo
Assistant Examiner—Mital Patel
(74) Attorney, Agent, or Firm—Dorsey & Whitney LLP

(57) ABSTRACT

A unitary breathing head device for administering intermittent percussive ventilation to a patient having an airway and for use with an IPV device having a source of continuous gas flow and having a source of pulsed gases comprising a combination injector and exhalation valve assembly comprising a main body having an airway port for communication with the airway of the patient and having proximal and distal extremities and a flow passage extending from the proximal extremity to the distal extremity. The main body has a depending portion forming a plenum chamber in communication with the flow passage in the main body. A nebulizer is removably secured to the depending portion of the main body and has a nebulizer chamber in communication with the plenum chamber. The depending portion of the main body and the nebulizer form a handle adapted to be gripped by the hand of the patient holding the breathing head assembly.

13 Claims, 4 Drawing Sheets

Figure 1:
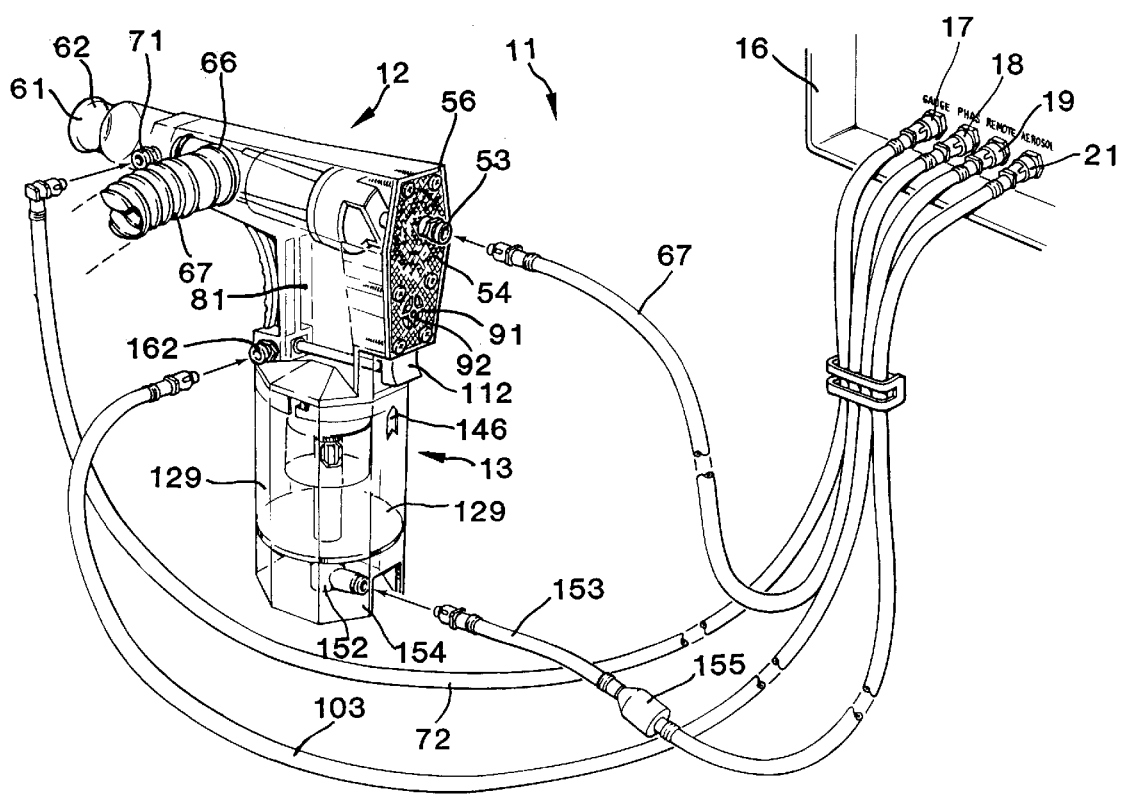

APPARATUS FOR ADMINISTERING INTERMITTENT PERCUSSIVE VENTILATION AND UNITARY BREATHING HEAD ASSEMBLY FOR USE THEREIN

This invention relates to an apparatus for administering intermittent percussive ventilation and to a unitary breathing head assembly for use therein.

As disclosed in U.S. Pat. No. 5,862,802 ventilators have heretofore been provided which have utilized in connection therewith combination exhalation valve and venturi assemblies as well as nebulizers. However, to meet present day applications for intrapulmonary percussive ventilation administered under institutional and domiciliary conditions to patients with chronic cardiopulmonary diseases and who often are decompensated with acute infections leading to a clinical decompensation, there is a need for a new and improved apparatus to meet these requirements.

In general, it is an object of the present invention to provide an apparatus and method for administering intermittent percussive ventilation which includes a unitary breathing head assembly.

Another object of the invention is to provide an apparatus of the above character in which the unitary breathing head assembly is provided with a removable nebulizer bowl for the insertion of medications, wetting agents, etc.

Another object of the invention is to provide an apparatus of the above character in which the interior of the unitary breathing head assembly can be readily accessed for cleansing purposes.

Another object of the invention is to provide an apparatus of the above character in which the unitary breathing head assembly is a semi-sealed unit with limited unsophisticated single unit disassembly to prevent loss of components.

Another object of the invention is to provide an apparatus having a unitary breathing assembly which makes it possible to easily flush out sterilization solutions to thereby prevent any retained sterilization agents from being nebulized into the patient's lungs.

Another object of the invention is to provide an apparatus of the above character in which the unitary breathing head assembly is located in close proximity to the physiological airway of the patient to enhance percussion as well as particulate aerosol delivery.

Another object of the invention is to provide an apparatus which includes a unitary breathing head assembly which can be readily held and operated by one hand of the patient.

Another object of the invention is to provide an apparatus of the above character in which the use of a spring has been eliminated in the unitary breathing head assembly.

Another object of the invention is to provide a unitary breathing head assembly which has the capability of backdraining coalescing microparticle (condensate) into the breathing head assembly while held in natural patient holding positions.

Another object of the invention is to provide an apparatus of the above character in which cyclic percussion can be initiated by a finger of a hand of a patient while the breathing head assembly is held in a normal position by the same hand of the patient.

Another object of the invention is to provide an apparatus of the above character in which constant nebulizer flow is provided.

Another object of the invention is to provide an apparatus of the above character in which interconnecting fittings have been greatly reduced to enhance clinical efficiency.

Another object of the invention is to provide an apparatus of the above character which can be economically manufactured.

Additional objects and features of the invention will appear from the following description in which the preferred embodiments are set forth in detail in conjunction with the accompanying drawings.

FIG. 1 is an isometric view of the apparatus for administering intermittent percussive ventilation incorporating the present invention and particularly showing the integrated breathing head assembly.

FIG. 2 is a side elevational view in cross section of the integrated breathing head assembly shown in FIG. 1 and showing the ambient entrainment gate in an open position.

FIG. 3 is a partial view of the integrated breathing head assembly showing means forming the cooperative mating mechanism permitting removal of the nebulizer bowl.

FIG. 4 is a view similar to FIG. 2 but showing dynamic nebulization without cyclic percussion.

FIG. 5 is another view similar to FIGS. 2 and 3 but showing dynamic nebulization with cyclic percussion.

In general, the apparatus for administering intermittent percussive ventilation is comprised of an intrapulmonary percussive ventilation device for providing sources of gases under continuous flow and cyclic flow and a unitary breathing head assembly, the unitary breathing head assembly being comprised of an elongate main body having proximal and distal extremities and having a flow passage extending from the proximal extremity to the distal extremity. The main body has an airway port adapted to be placed in communication with the airway of the patient and in communication with the flow passage. An expiratory port is carried by the main body proximal of the airway port. A valve seat is formed in the main body and circumscribes the flow passage in the main body. An injector body is slidably mounted in the flow passage and is movable into and out of engagement with the valve seat. A yieldable diaphragm is carried by the main body and engages the injector body and yieldably urges the venturi body out of sealing engagement with the valve seat. The injector body has a venturi-like passage extending therethrough. The main body is provided with a depending portion forming a plenum chamber in communication with the flow passage in the main body. A nebulizer is provided which has a nebulizer bowl forming a nebulizer chamber. Cooperative mating means is provided for removably securing the nebulizer bowl to the depending portion of the main body to establish communication between the nebulizer chamber and the plenum chamber. Tubing is provided for coupling the intrapulmonary percussive ventilation device to the nebulizer and the main body for supplying a continuous flow of gas to the nebulizer and a pulsatile flow of gases to the main body.

More in particular as shown in the drawings, the apparatus 11 for administering intermittent percussive ventilation to a patient consists of a combination injector and exhalation valve assembly 12, a prior embodiment of which was identified as a "Phasitron", trademark, and an integral nebulizer 13 forming a unitary breathing head assembly 14 coupled to an intrapulmonary percussive ventilation (IPV) device 16. The IPV device 16 can be one of a family manufactured and sold by Percussionaire Inc. of Sandpoint, Id., which is provided with a plurality of fittings 17, 18, 19 and 21 which can be identified respectively as a "gauge", "Phasitron", "remote" and "aerosol" and which provides a continuous flow of gas from the aerosol fitting 21 and a cyclic source of gas from the Phasitron fitting 18.

The combination injector and exhalation valve assembly 12 consists of a hollow elongate body 26, generally rectangular in cross section, having proximal and distal extremities 27 and 28 and a flow passage 29 extending from the proximal extremity to the distal extremity. The flow passage 29 is provided with step reductions at 31 and 32 in which the step reduction 32 serves as a circular valve seat which circumscribes the flow passage 29. An injector body 36 is slidably mounted in the flow passage 29 and has proximal and distal extremities 37 and 38. Cooperative sealing means is provided between the distal extremity 38 of the injector body 36 and the valve seat 32 and takes the form of valve member 39 and an o-ring 41 provided on the distal extremity 38 of the injector body 36 and positioned so that a fluid-tight seal can be formed between the distal extremity of the injector body 36 and the valve seat 32. A venturi-like passageway 42 having an entrainment port 43 is formed in the injector body 36 and extends from the proximal extremity 37 to the distal extremity 38. An end cap 46 is mounted on the proximal extremity 37 of the injector body 36 and is mounted thereon by suitable means such as a threaded connection 47. The side portions of the end cap 46 have been cut away to provide openings 48 on opposite sides of the end cap.

Means is provided for engaging the injector body 36 and for yieldably retaining the injector body in an open position with respect to the valve seat 32 and takes the form of a diaphragm 51 having a retracting memory. A venturi orifice 52 is mounted in the end cap 46 and is in alignment with the venturi-like passageway 42. The venturi orifice 52 is coupled to the center of the diaphragm 51 and is in communication with an inlet fitting 53 carried by an end plate 54 mounted on the proximal extremity 27 of the body 26. End plate 54 is secured to the body 26 by a suitable means such as screws 56. Fitting 53 is connected by tubing 61 (see FIG. 1) to the Phasitron terminal 18 of the IPV device 16.

The distal extremity 28 of the body 26 is formed to provide a mouth piece 61 which is adapted to be engaged by the lips of the patient when the mouth piece 61 is disposed within the mouth and airway of the patient. As can be seen the mouth piece 61 is provided with an annular recess 62 which is adapted to accommodate the lips so that a fluid-tight seal can be formed between the lips of the user or patient and the body 26. By molding the annular recess 62 in the mouth piece 61 as an integral component of the body 26 rather than utilizing a separate mouth piece makes it possible to eliminate obstructive circumferential step-downs which would be created by insertion of a mouth piece into the passageway. This aids in reducing turbulent precipitation of the aerosol being transported by the gaseous vehicle from the venturi-like passageway 42 into the airway of the patient.

An exhalation port 66 is provided on the body 26 just proximal of the valve seat 31 and extends sidewise therefrom and is in communication with the flow passage 29. A short piece of corrugated tubing 67 is mounted on the exhalation port 66 and serves to collect any liquids which may condense from the gases exhaled through the exhalation port 66. The exhalation port 66 is angled away at substantially right angles to the flow passage 29 to ensure that any airborne aerosol particles exiting through the exhalation port clear the patient's face. The wide bore tubing 67 provided on the exhalation port 66 serves dual purposes. One, it is a reservoir for collecting aerosol that escapes from the exhalation port during the inspiratory phase and/or during percussive cycling. During inhalation, the aerosol can be recovered from the reservoir provided by the tubing and cause it to re-enter the passageway to the airway of the patient. In addition, the tubing 67 serves to prevent the aerosol exiting through the exhalation port from contaminating the surroundings of the patient.

Means is provided for sensing the pressures encountered within the flow passage 29 distal of the valve seat 32 and proximal of the mouth piece 61 and consists of a fitting 71. This fitting 71 is connected by tubing 72 to the gauge terminal 17 of the IPV device 16.

The injector and exhalation valve assembly 12 also includes a depending housing 81 which is formed integral with the body 26 and is substantially rectangular in cross section in a horizontal plane and defines a plenum chamber 82 which opens upwardly through an opening 83 to communicate with the flow passage 29. The rear or proximal side of the housing 81 is provided with an opening 86 in which there is mounted an ambient entrainment gate in the form of a flapper valve 87. This opening 86 is overlaid with the end plate 54. The lower portion of the flapper valve 87 is formed of a flexible yieldable material and has its lower extremity bonded to the lower extremity of the end plate 54 by suitable means such as an adhesive (not shown). The upper extremity because of the memory of the material is yieldably urged into engagement with the end plate 54 to normally close the opening 86. The flapper valve 87 which serves as the ambient entrainment gate can be have a suitable configuration as for example circular. The end plate 54 is provided with an opening 91 generally in alignment with the opening 86 and is normally closed by the flapper valve 87(see FIG. 4). A web 92 of reinforcing portions formed integral with the end plate 54 are disposed in the opening 91 and serves to provide support so that the flapper valve 87 cannot inadvertently pass rearwardly through the opening 91. Thus, the flapper valve 87 can only move from a sealing relationship with respect to the opening 91 to permit ambient air to pass into the opening 86 by movement of the upper extremity of the flapper valve 87 inwardly as shown in FIG. 2.

The forward extremity of the depending housing 81 is provided with a serrated curved surface 96 adapted to be engaged by a finger of a hand as for example the thumb of the hand holding the device 14.

A chamber 101 is formed in the lower extremity of the housing and has a fitting 102 mounted in the housing and in communication with the chamber. The fitting 102 is connected by tubing 103 (see FIG. 1) to the remote terminal 19 of the IPV device 16. The chamber 101 is also provided with an opening 106 in communication with the chamber 82 of the depending housing 81 and is circumscribed by a circular valve seat 107. The valve seat 107 is adapted to be engaged by a valve member 108 carrying an o-ring 109. The valve member 108 is carried by a valve stem 111 that extends through the rear wall of the housing 81 which has formed integrally thereon a push button 112 adapted to be engaged by the finger of a hand holding the device as for example the index finger as herein described. Means is provided for yieldably urging the valve member 108 into engagement with the valve seat 107 and consists of upper and lower oppositely disposed spring fingers 113 and 114 formed integral with the push button 112 but having opposite extremities relieved so that these spring fingers 113 and 114 can be depressed against the wall of the housing 81 to yieldably move the valve member 108 out of engagement with the valve seat 107 to prevent cyclic percussion as hereinafter described. As soon as the push button 112 is released, the spring fingers 113 and 114 will move the valve member 108 into a closed position with respect to the valve seat 107.

The nebulizer 13 is removably secured to the lower extremity of the depending housing 81. Cooperative mating and sealing means 121 is provided for securing the nebulizer 13 to the depending housing 81 and forming a sealing engagement therewith. This cooperative securing and sealing means 121 as shown in FIG. 3 takes the form of a circular rim 122 provided on the lower extremity of the housing 81 and carries an o-ring 123. The nebulizer 13 is provided with a bowl 126. The bowl 126 is provided with an arcuate or disk-shaped bottom wall 127 and an upstanding multifaceted exterior side wall 128. The outer surface of the side wall 128 can be provided with a plurality of facets 129 (see FIG. 1) as for example eight to facilitate grasping of the bowl 126 when securing it to and removing it from the depending housing 81. The upstanding side wall 128 is provided with a smooth inner cylindrical surface 131 and defines a cylindrical chamber 132 which opens upwardly and is in communication with the chamber 82 in the depending housing 81.

Figure 3:
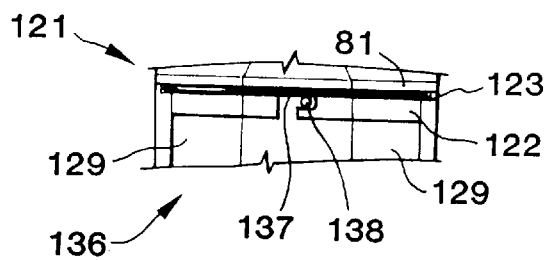

A suitable twist lock connection 136 is provided for removably securing the nebulizer 13 to the depending housing 81 and consists of a pair of L-shaped slots 137 (see FIG. 3) formed on opposite sides of the rim 122 which are adapted to receive and be engaged by a pair of pins 138 carried on opposite sides of the exterior cylindrical surface of the bowl 126. Thus it can be seen that by moving the bowl 126 upwardly so that the pins 138 are in registration with the L-shaped slots 137 provided in the rim 122, the upstanding side wall 128 can be pushed into engagement with the o-ring 123, at which time the bowl 126 and the depending housing 81 can be rotated with respect to each other to cause the pins 138 to seat in the sidewise extending leg of the L-shaped slot 137 to firmly retain the bowl 126 in sealing engagement with the o-ring 123 carried by the rim 122 of the depending housing 81.

The bowl 126 is provided with a depending skirt 141 which has a lower planar surface 142 that is adapted to rest upon a flat surface such as provided by a table to facilitate filling of the bowl 126. One of the facets 129 is provided with an arrow 146 to indicate the direction in which the bowl 126 is to be moved to secure the same to the depending housing 81. In addition, one of the facets 129 can be provided with indicia (not shown)indicating 10, 15 and 22 cc levels, respectively, within the bowl to facilitate filling the bowl 126 with an appropriate amount of liquid.

Figure 4:
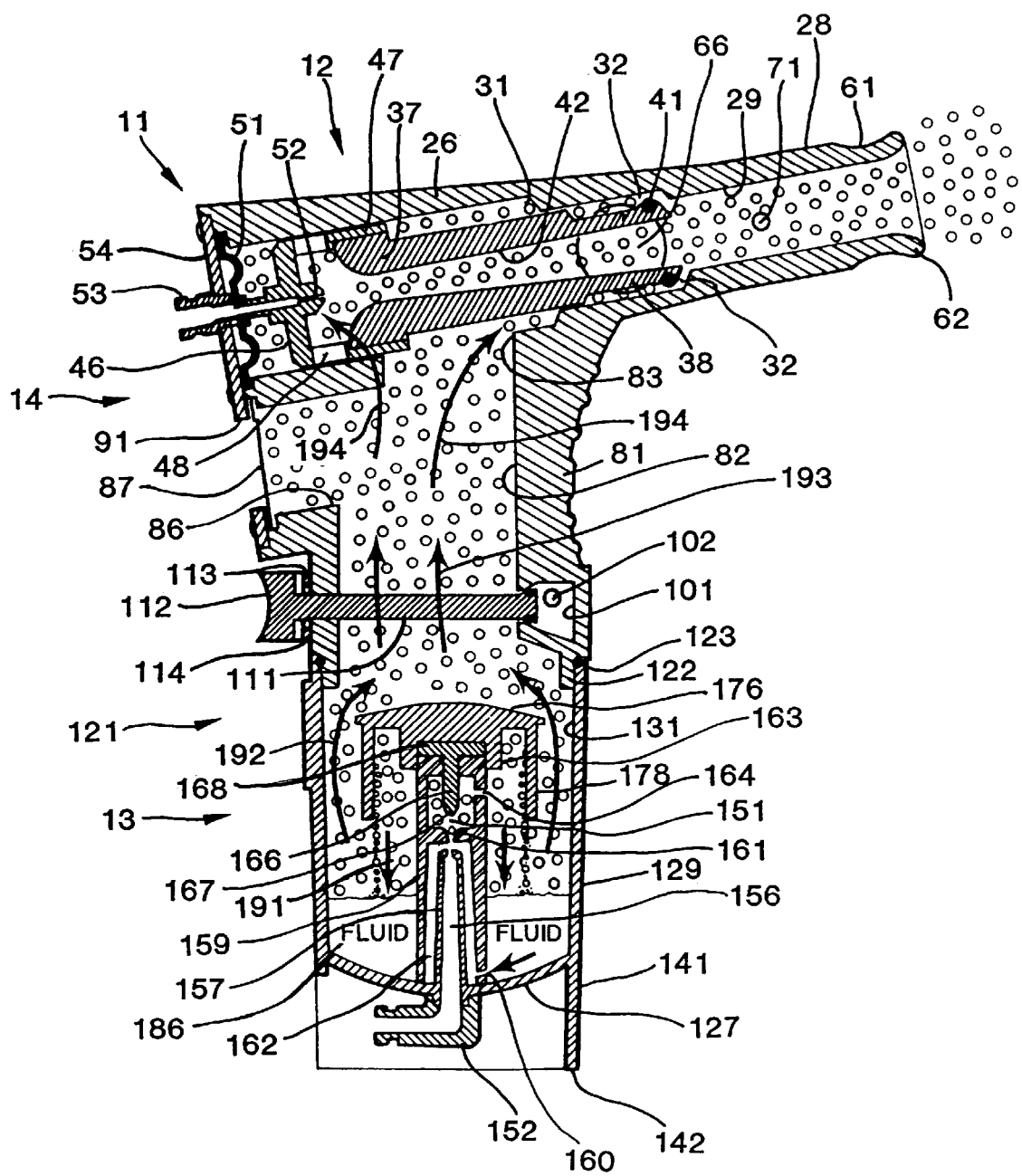
Figure 5:
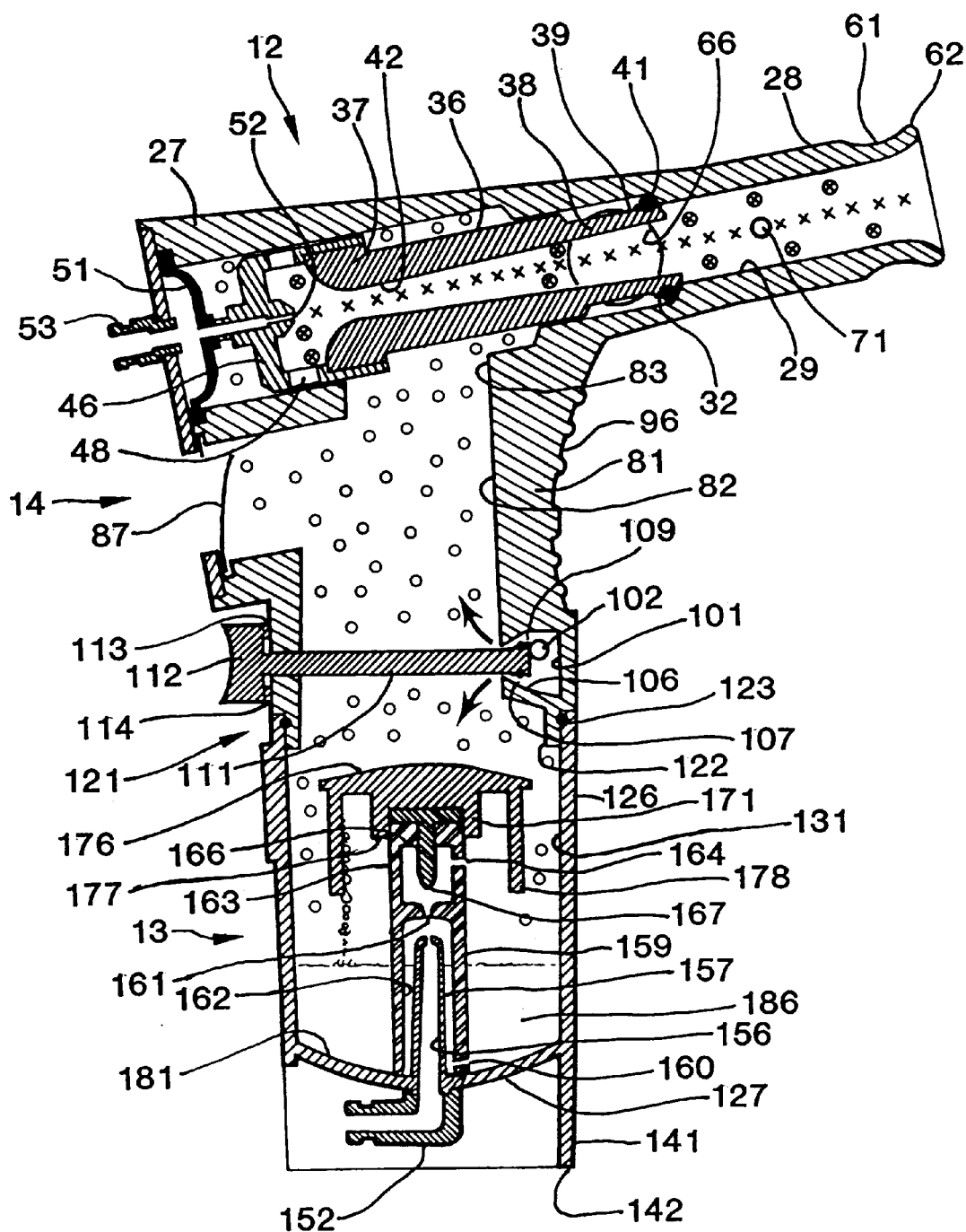

Nebulizing means 151 is provided within the bowl 126 of the nebulizer 13 and is connected to an L-shaped fitting 152 which is adapted to be connected to tubing 153 (see FIG. 1) extending through a recess 154 in the depending skirt 141 and which includes a check valve 155. The tubing 153 is connected to the aerosol fitting 21 provided on the IPV device 16 through a check valve 155. The fitting 152 is in communication with a bore 156 provided in an upstanding post 157 centrally disposed within the cylindrical chamber 132 of the bowl 126. A sleeve 159 is removably mounted over the post 157 and is provided with a bore 161 in registration with the bore 156. A flow passage 162 is provided between the post 157 and the interior of the sleeve 159 for bringing liquid from the bowl 126 through side openings 160 and mixing it with the air, through the bore 156 and exiting through the orifice 161. The sleeve 159 is provided with an integral shroud 163 having openings 164 therein. A diffractor plug 166 is adjustably mounted in the shroud 163 and is provided with a downwardly facing convex surface 167 that overlies the orifice 161 and is utilized for diffraction of the aerosol exiting through the orifice 161. The diffractor plug 166 is provided with a knurled cap 171 which can be used for inserting and removing the plug and alternatively for adjusting the position of the convex surface 167 of the plug with respect to the orifice 161.

A contouring cape 176 is removably mounted on the upper extremity of the sleeve 159 and overlies the knurled cap 171 of the diffraction plug 166. The contouring cape 176 has an inner depending cylindrical skirt 177 which makes a snap-on friction fit with the upper extremity of the sleeve and the knurled cap 171 to hold the contouring cape 176 in position within the nebulizer bowl 126. The contouring cape 176 is also provided with an outer cylindrical depending skirt 178 which extends downwardly into the bowl 126 and which is at least below the lower extremities of the openings 164 provided in the shroud 163. The contouring cape 176 is provided with an outer disk-shaped upper surface 181 which has its outer perimeter terminating at the outer depending skirt 178.

The depending portion 81 of the main body 26 and the attached nebulizer 13 form a handle which can be grasped by a patient during use of the device 14.

Operation and use of the apparatus 11 for administering intermittent percussive ventilation to a patient may now be briefly described as follows. Rather than inserting the mouth piece 61 into the mouth of a patient it is possible to place a cylindrical adapter within the mouth piece 61 and connect the same to a conventional inflatable face mask which can be held in place in a conventional manner on the face of a patient during therapy utilizing the apparatus of the present invention.

Let it be assumed that the patient desires to take a treatment. The patient for example may grasp the device 14 by the left hand and then grasp the nebulizer bowl 13 by the right hand and rotate the nebulizer counterclockwise a small amount until the downwardly dependent leg of the L-shaped slot is encountered to permit the bowl 126 to be retracted and released. The bowl can then be placed on a table or other support surface (not shown) with the lower surface 42 of the depending skirt 141 resting on the support surface. An appropriate amount of liquid as for example 20 cc's of water can be placed in the chamber 132 of the bowl and an appropriate amount of medication placed therein as for example six drops of a desired medication. While holding the device 14 in the left hand, the right hand of the patient can be utilized to lift the bowl 126 and to insert the pin 138 into the L-shaped slots and then rotate the bowl 126 clockwise with respect to the depending housing 81 to form a fluid-tight seal between the bowl 126 and the housing 81. Tubing 153 is then connected to the fitting 21 to provide a continuous flow of gas from the IPV device 16 to the nebulizer. Tubing 61, 72 and tubing 103 are connected to the fittings 53, 71 and 102 respectively and in turn connected to the terminals 18, 17 and 19 of the IPV device 16. The device is now ready for use.

The patient can pick up the device 14 by grasping the nebulizer 13 by the right hand and bringing the mouth piece 61 to the mouth of the patient and introducing it into the mouth of the patient so that the lips of the patient form a substantially air-tight seal with respect to the recess 62. The condition which exists in the device 14 at this time is shown in FIG. 4 in which there is dynamic nebulization in a nebulizer 13. A constant flow of source gas is supplied to the fitting 152 from the tubing 153. Gas of a pressure of for example 40 psi is supplied to nebulizer 13 fractionates the liquid 186 in the bowl 126 which is being drawn up into the passage 162 into particles having a mean average size of approximately 7 microns. The nebulizer of the size shown can have an output of approximately 120 milliliters an hour. In other words when a pressurized gas is introduced into the fitting 152, gas passes through the bore 156 and through the bore 161 and causes liquid to be extracted from the reservoir or chamber 132 and to be drawn up the passage 162 by capillary attraction and thence be introduced into the air which is exiting from the bores 156 and 161 to impinge upon the convex surface of the diffraction plug 166 to cause the liquid entrained in the air to be broken up into very small droplets. These droplets are discharged downwardly as indicated by the arrows 191 after impinging upon the depending skirt 178 after which the aerosol strikes the surface of the liquid 186 and passes upwardly as indicated by the arrows 192 into the plenum chamber 82 as indicated by arrows 193 and thence into the flow passage 29 and also as indicated by the arrows 194 into the openings 48 provided in the end cap 46. The aerosol then passes into the venturi-like passageway 42 and thence into the passageway 29 into the mouth piece 61 and into the airway of the patient to begin inflation of the lungs of the patient during commencement of the inspiratory phase. In addition aerosol passes around the injector body 36 through the open valve seat 32 into the passageway 29 into the airway of the patient as shown in FIG. 4. The rectangular plenum surrounding the injector body 36 provides a proximal and a distal venturi bypass route for aerosols to travel around the exterior injector body directly pass the o-ring gate 41 to be entrained into the physiological airway during spontaneous respiration of the patient. This arrangement makes it possible to provide enhanced therapeutic aerosol delivery when the breathing head device 14 is being utilized as a nebulizer only.

Thereafter to continue with the inspiratory phase with cyclic percussion, the patient depresses the push button 112 against the yieldable force of spring fingers 113 and 114 to move the valve member 108 away from the valve seat 107 to vent the chamber 101 to the plenum chamber 82. As soon as this occurs, pulses of gas are supplied from the terminal 17 of the IPV device 16 through the tubing 61 to the fitting 53 to overwhelm the venturi orifice 52 and thereby inflate the space between the diaphragm 51 to overcome the retractive force of the memory in the diaphragm 51 and to thereby cause movement of the injector body 36 in a distal direction to move the valve member 39 carried by the distal extremity of the injector body 36 and carrying the o-ring 41 into engagement with the valve seat 32 to close off the exhalation port 66. The pulsatile gases are supplied from the venturi orifice 52 through the venturi-like passageway 42 and thence into the airway of the patient through the mouth piece 61. During the supply of these pulsatile gases to the fitting 53, the pulsatile gases repeatedly move the injector body 36 between closed and open positions with respect to the valve seat 32 to close and open the exhalation port 66. Although expiratory gases are released through the exhalation port 66 upon each opening of the exhalation port, there is only a partial release of the gas from each cyclic pulse until a maximum inflated pressure is reached. As soon as a pulse of gas is terminated to the fitting 53, the diaphragm 51 with its retracting memory returns the injector body 36 to its rearmost position to again open the expiratory port 66 to provide a partial release of expiratory gases. Thus there is a rapid opening and closing of the expiratory port 66 in accordance with the frequency of the pulsatile gases at cyclic rates ranging from 120 to 420 cycles per minute. Typically the lungs of the patient can be filled to a maximum pressure in 6 or 10 cycles. Cyclic pulsing is continued to provide cyclic pulsing of the gases against the lungs of the patient. The maximum pressure applied to the lungs is limited by the pneumatic clutching provided by the venturi-like passageway 42. Thus, it can be seen that the lungs of the patient are step inflated to a maximum pressure and then the lungs are continued to be percussed during the inhalation phase. During such percussing, the gases are mechanically mixed in the lung.

When the patient desires to exhale, the patient merely needs to exhale against the incoming pulsatile gases and creates a pressure against the diaphragm 51 to overwhelm the forces being applied to the diaphragm to move the o-ring 41 and the valve member 39 away from the valve seat 32 permitting the patient to exhale through the exhalation port 66. The patient can exhale any time the patient desires to exhale. After the valve member 39 with its o-ring 41 is moved off of the valve seat 32 with commencement of exhalation, the retracting memory provided by the diaphragm 51 retains the injector body 36 in a retracted position.

After exhalation has been completed, the pressure drops within the passageway 29 and the pressures created by the pulsing gases supplied to the fitting 53 again overwhelm the diaphragm and again cause the injector body 36 to move forwardly or distally to cause the valve member 39 with its o-ring 41 to come into engagement with the valve seat 32.

Figure 2:
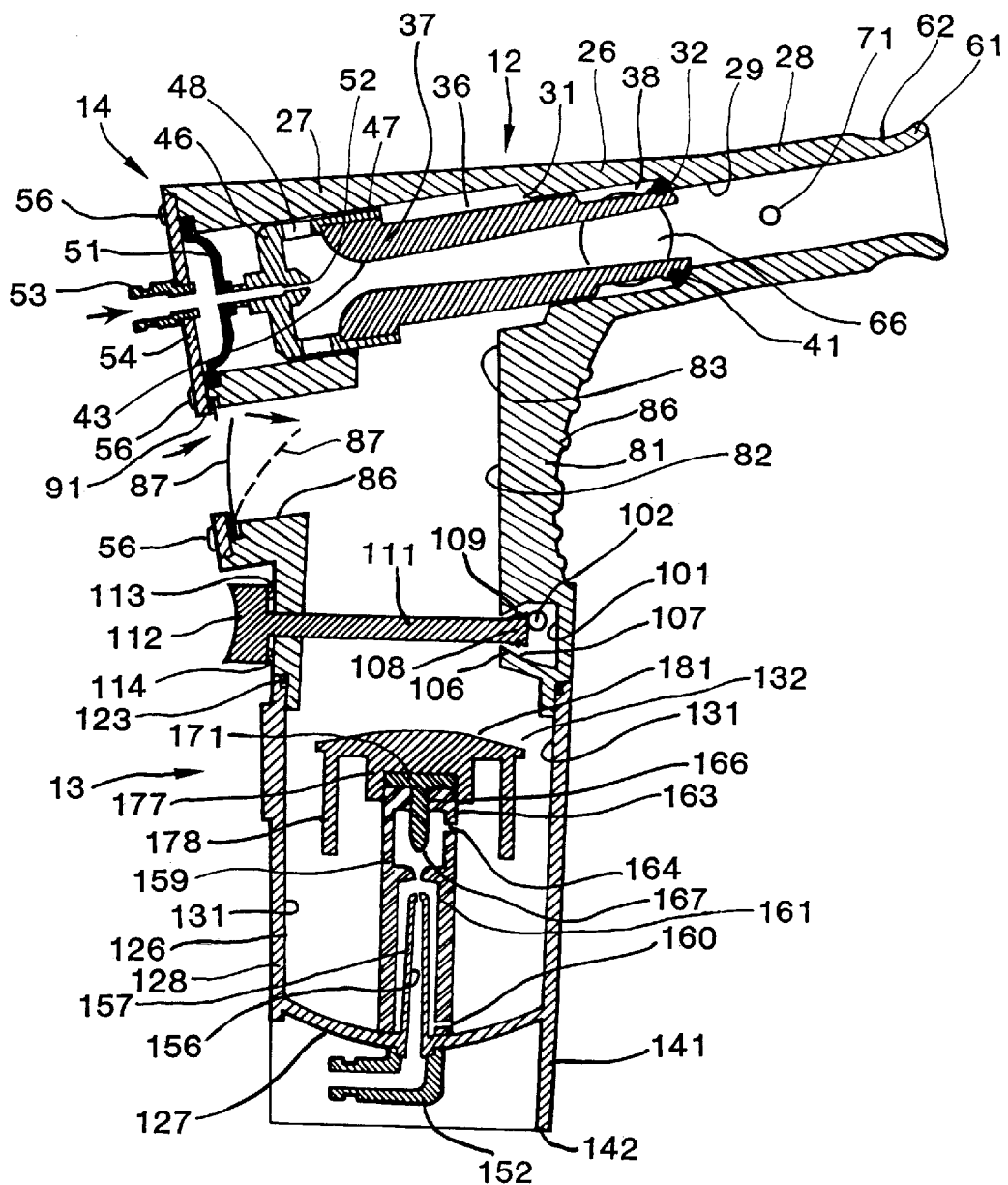

During the inhalation phase at any time that the demand of the patient exceeds the outflow from the nebulizer 13, ambient air is introduced for mixing with the aerosol being supplied by the nebulizer 13 through the flapper valve 87 serving as an ambient entrainment gate by movement to the dotted line position shown in FIG. 2. In this manner ambient air is aspirated into the plenum chamber 82 which is already loaded with a supersaturated aerosol. This entrainment of ambient air provides means to greatly enhance uninterrupted therapeutic aerosol delivery during the inspiratory phase at near the immediate start of percussive injection of pulsatile gases into the airway of the patient. When the physiological airway pressure increases to or beyond the selected fluid clutching (venturi stalling) pressure within the injector body 36, the ambient entrainment gate 87 closes and prevents any ambient aerosol flushing from the plenum chamber 82 between the nebulizer 13 and the entrainment port 43 of the venturi-like passageway 42 and to maintain a potential directional flow of aerosol upward and around the injector body 36 to ambient through the exhalation port at all times. A pressure of −10 to −15 mm HG is maintained in the throat of the venturi-like passageway with the pulsed gas supplied to the venturi orifice 52 at 10 to 15 PSIG.

With the breathing head assembly 14 of the present invention it is possible to maintain a constant source of uninterrupted aerosol flow past the entrainment port 43 of the venturi-like passageway 42 for inspiratory aspiration during flow reversals or transitions within the injector body 36 and against changing intrapulmonary resistances. Therefore aerosol can flow (under a slight pressure gradient) from the nebulizer bowl 136 through the plenum chamber to around the injector body 26 to ambient during the venturi flow reversals. For that reason means is provided to maintain a supersaturated gas delivery into the physiological airways throughout the gas injection period as transient physiological air inflow rates are widely varied.

The pulsatile inflow of gases from the dynamic timing circuit chamber 101 into the aerosol plenum chamber 82 provides an additional means for augmenting the gaseous vehicle within the plenum chamber 82 which is employed to transport dense aerosol particles through the venturi entrainment port for delivery to the venturi-like passageway 42 into the physiological airways of the patient.

When the nebulizer bowl 126 is in a substantially vertical position with its bottom surface 142 being horizontal, the lower surface of the body 26 is inclined downwardly and rearwardly at a suitable angle as for example 20 to 40 degrees to provide a backward inclined slant when the device 14 is held by a patient's hand with an elbow of the arm of the hand resting on the arm of a chair or a bed. The inclination provides means whereby any aerosol which has coalesced because of turbulence and thermal gradients within the venturi-like passageway 42 and/or within the passageway 29 will flow by force of gravity to return through the plenum chamber 82 and thence into the nebulizer bowl 126.

The regulated continuous inflow from the nebulizer 13 transports an aerosol having aerosol particles therein into the combination injector and exhalation valve assembly herein called the Phasitron for delivery to the physiological airway of the patient. The entrainment port 43 of the injector body 36 is initially supercharged to provide aerosol flooding which enhances delivery volume of the aerosol to the patient and also serves to increase the amplitude of the serialized percussive inspiratory and expiratory pulses of gas supplied to the venturi-like passageway 42 of the injector body 36. This initial supercharging and the follow-on flooding of the entrainment port 43 serves as a means to augment the intrapulmonary aerosol delivery during percussive step inflation of the lungs of the patient. This greatly enhances the peripheral delivery of bronchodilators, wetting agents, vasoconstrictor medications and the like into the pulmonary airways of the patient in accordance with airway clearance protocols. Vaccines and other immunological agents can also be similarly delivered endobronchially.

The contouring cape 176 snaps over the top of the diffractor cap 171 and makes it possible to more precisely control the particulate size and volume of aerosol generation in the nebulizer 13. By determining the diameter of and length of the skirt 178 it is possible to control the output as well as the particulate spectral output of the nebulizer 13 throughout the operational pressure range. This is made possible by appropriate placement of the depending skirt 178 to control the distribution of aerosolized spray from the openings 164 of the shroud 163 by selecting particulate impaction angles including swirl and secondary rain-out so that they impact against the inner walls of the depending skirt 178. The inner surface of the depending skirt 178 can be smooth, serrated irregular or hatched as desired to control particulate spectrum and output volumes at constant or differing operational pressures. The downward protrusion of the depending skirt 178 with respect to the jet capillary junction at the convex surface 167 of the diffraction plug 166 provides means for determination of the downward diffusive deflection of undesirable superaerosol particles and causing them to re-enter the solution. The other aerosol particles follow a circuituous predetermined escape route around the inner surface of the depending skirt 178 and thence upwardly into the plenum chamber 82 for subsequent venturi entrainment. The spacing provided within the depending skirt 178 makes it possible to influence impacting coalescing and secondary rain-out of aerosol spray by providing means for regulation of the aerosol emission volume. A major role of the depending skirt 178 is to provide a means for decreasing "spitting" (creation of unprogrammed superparticles) which could enter and coalesce within the plenum chamber 82 and within the venturi-like passageway 42. It should be appreciated that different sizes of contouring capes 176 can be provided. By using different geometric configurations it is possible to control microparticle spectrums and volumes specific to various endobronchial aerosolized solution deliveries to a patient even though using the same nebulizer 13.

During operation of the device 14, condensation and evaporation within the nebulizer bowl 126 and the plenum chamber 82 to resolve the humidity deficit as the aerosol gaseous transporting vehicle becomes saturated by molecular release from the aerosol particles, a moderate temperature drop occurs. With dry oxygen (low relative humidity), the bowl temperature can drop by as much as 15 or more degrees F. This temperature drop increases the density of the gaseous transport vehicle, making it possible to transport additional aerosol particles.

As the transporting gaseous aerosol vehicle (air/oxygen) enters the aerosol mixing plenum chamber 82, a progressive warm-up occurs until a 37° C. and/or physiological respiratory tract temperature is reached. During this progressive warm-up, the gaseous vehicle expands requiring additional water molecules to maintain saturation. The water molecules are released (sloughed) from the dense aerosol particles, to accommodate the molecular demand. Therefore the particulate spectrum can be upwardly adjusted by use of different size capes to accommodate the physiological humidity deficit and still maintain a desirable particulate spectrum for diffuse therapeutic or immunologic endobronchial delivery.

When it is desired to supply supplemental oxygen to the airway of the patient to control the amount of ambient air, the ambient entrainment gate 87 can be closed off. This ensures that the source of respiratory gas will determine the oxygen concentration. Thus without an ambient gas entrainment, the concentration of oxygen as well as aerosol delivered into the airway of the patient is enhanced.

When the patient desires to exhale against the incoming pulsatile gases, the patient uses the patient's lungs to create an overwhelming back pressure within the throat of the venturi-like passageway 42, thereby exceeding the mean fluid catching pressures within the throat, permitting the patient to exhale through exhalation port 66 between cyclic gas injections. The patient can also exhale at any desirable time by forcefully overcoming the mean venturi throat pressure. After the valve member 39 with its o-ring 41 is moved off of the valve seat 32 with commencement of exhalation, the retracting memory provided by the diaphragm 51 retains the injector body 36 in a retracted position.

Whenever a patient is to terminate the flow of pulsatile gases to the injector body 36, the patient need merely release the push button 112. This closes the chamber 101 and prevents further delivery of pulsed gases to the injector body 36.

When the patient has finished the desired treatment, the mouth piece 61 can be removed from the mouth of the patient and the supply of gases to the nebulizer 13 is terminated by operation of the IPV device 16.

The breathing head device 14 is formed principally of plastic components. Thus the nebulizer 13 can be separated from the combination injector and exhalation valve 12 and the various components can then be backwashed mechanically and positioned to drain by gravity. It thus can be seen that the construction of the device 14 makes it possible to mechanically wash out and cleanse all internal components to maintain maximal clinical efficacy.

From the foregoing it can be seen that an apparatus has been provided which utilizes a unitary breathing head device 14 which includes a combination injector and exhalation valve assembly with a nebulizer formed integral therewith. The breathing head assembly can be readily accessed for cleaning purposes. The breathing head assembly is a semi-sealed unit with a limited unsophisticated single unit disassembly to prevent loss of components. The breathing head assembly is located in close proximity to the physiological airway of the patient to enhance percussion as well as particulate aerosol delivery. The integrated breathing head assembly makes it possible to be held and operated by a single hand of the patient. The breathing head assembly is constructed to facilitate backdraining of coalescing microparticles into the breathing head assembly while held in natural patient holding positions. Since the breathing head assembly is substantially all fabricated from plastic, it can be economically manufactured. The construction has been greatly simplified to enhance ease of use by the patient.

What is claimed:

1. Apparatus for administering intermittent percussive ventilation to a patient having an airway, comprising an intrapulmonary percussive ventilation device for providing sources of gases under continuous flow and cyclic flow and a unitary breathing head assembly, the assembly comprising an elongate main body having proximal and distal extremities and having a flow passage extending from the proximal extremity to the distal extremity, the main body having an airway port adapted to be placed in communication with the airway of the patient and in communication with the flow passage of the main body, an expiratory port carried by the main body proximally of the airway port, a valve seat formed in the main body and circumscribing the flow passage in the main body, an injector body slidably mounted in the flow passage of the main body and having proximal and distal extremities, the injector body having its distal extremity movable into and out of engagement with the valve seat, the injector body having a passageway extending therethrough from the proximal extremity to the distal extremity, a diaphragm carried by the main body coupled to the injector body having a retracting memory for retaining the injector body in a retracted position with respect to the valve seat, the main body having a depending portion forming a plenum chamber in communication with the flow passage in the main body, a nebulizer having a nebulizer bowl providing a nebulizing chamber therein, cooperative mating means for removably securing the nebulizer body to the depending portion of the main body and establishing communication between the nebulizing chamber and the plenum chamber in the depending portion of the main body, and tubing coupling the intrapulmonary percussive ventilation device to the nebulizer and to the main body for supplying a continuous flow of gas to the nebulizer and a pulsatile flow gas to the main body.

2. Apparatus as in claim 1 wherein said depending portion has an ambient entrainment gate therein for mixing ambient air with the aerosol in the plenum chamber.

3. Apparatus as in claim 1 for use with a horizontal support surface wherein said nebulizer is provided with a depending skirt having a lower extremity lying in a horizontal plane, said depending skirt having dimensions whereby the breathing head assembly is supported in an upright position when the lower planar surface is resting on the horizontal support surface.

4. Apparatus as in claim 1 wherein said main body has a lower surface which is inclined downwardly and rearwardly so that liquid condensing within the passageway in the main body and in the passageway will flow by force of gravity through the plenum chamber into the nebulizer chamber of the nebulizer bowl.

5. Apparatus as in claim 1 wherein said nebulizer bowl is provided with liquid therein, a shroud mounted in the nebulizer bowl and extending above the liquid, a diffractor surface carried by the shroud, capillary means in the shroud for delivering liquid from the liquid in the nebulizer bowl and causing it to impinge against the deflector surface to provide an aerosol emitted from the shroud, and a cape carried by the shroud and being mounted over the diffractor surface and having a depending skirt, said depending skirt serving to control the dispersion of the aerosol being emitted from the shroud.

6. Apparatus as in claim 5 wherein said cape is removable so that it can be interchanged.

7. Apparatus as in claim 1 further including switch means including a push button carried by the depending portion adapted to be engaged by a finger of the hand holding the breathing head device for controlling the flow of pulsatile gases to the main body.

8. A unitary breathing head device for administering intermittent percussive ventilation to a patient having an airway and for use with an IPV device having a source of continuous gas flow and having a source of pulsed gases comprising a combination injector and exhalation valve assembly comprising a main body having proximal and distal extremities and a flow passage extending from the proximal extremity to the distal extremity, said main body having an airway port carried by the main body at the distal extremity thereof and in communication with the flow passage in the main body, an expiratory port carried by the main body proximal of the airway port, a valve seat formed in the main body and circumscribing the flow passage in the main body, an injector body slidably mounted in the flow passage of the main body and having proximal and distal extremities and having its distal extremity movable into and out of engagement with the valve seat, the injector body having a passageway extending therethrough from the proximal extremity to the distal extremity, a diaphragm carried by the main body and coupled to the injector body, the main body having a depending portion forming a plenum chamber in communication with the flow passage in the main body, the breathing head device also comprising a nebulizer, the nebulizer comprising a nebulizer bowl having a nebulizer chamber therein, cooperative mating means for removably securing the nebulizer bowl to the depending portion of the main body and establishing communication between the nebulizer chamber and the plenum chamber, the depending portion of the main body and the nebulizer forming a handle adapted to be gripped by the hand of the patient holding the breathing head device during use, a fitting connected to the nebulizer which is adapted to be supplied with a continuous flow of gas from the IPV device and a fitting connected to the main body which is adapted to be supplied with pulsed gases from the IPV device for delivery to the diaphragm and to the injector body.

9. A breathing head device as in claim 8 for use with a horizontal support surface wherein said nebulizer is provided with,a depending skirt, a surface lying in a horizontal plane for supporting the breathing head device in an upright position when the depending skirt of the nebulizer is resting upon the horizontal support surface.

10. A breathing head device as in claim 8 further including switch means carried by the depending portion of the main housing for controlling the supply of pulsed gases to the main body.

11. A breathing head device as in claim 8 wherein said diaphragm has a retracting memory whereby the injector body is yieldably maintained out of engagement with the valve seat.

12. A breathing head device as in claim 8 wherein said nebulizer has a liquid therein and nebulizing means within the bowl for aspirating liquid from the bowl and creating an aerosol containing liquid particles therein.

13. An assembly as in claim 12 further including a cape having a depending skirt overlying the nebulizing means and carried by the nebulizing means.

* * * * *